United States Patent
Johnston et al.

(10) Patent No.: US 7,562,556 B2
(45) Date of Patent: Jul. 21, 2009

(54) CLEANING SYSTEM AND METHOD FOR CONTINUOUS EMISSIONS MONITORING EQUIPMENT

(75) Inventors: David F. Johnston, Poquoson, VA (US); Jennifer Lynn Molaison, Marietta, GA (US); Terry Farmer, Kearney, MO (US); William Eberhardt, Cherry Hill, NJ (US); Mark Holt, Emmaus, PA (US)

(73) Assignee: General Electric Company, Schenectady, NY (US)

( * ) Notice: Subject to any disclaimer, the term of this patent is extended or adjusted under 35 U.S.C. 154(b) by 190 days.

(21) Appl. No.: 11/541,970

(22) Filed: Oct. 2, 2006

(65) Prior Publication Data

US 2008/0078260 A1   Apr. 3, 2008

(51) Int. Cl.
*B08B 9/027* (2006.01)
*B08B 7/02* (2006.01)
*G01N 1/22* (2006.01)
*F23J 3/00* (2006.01)

(52) U.S. Cl. .............. 73/23.31; 15/94; 15/104.05; 15/406; 73/863.81; 134/22.1; 134/166 C

(58) Field of Classification Search ............. 73/24.01, 73/432.1, 570, 866.5, 23.31, 863.81; 95/3, 95/11, 29; 96/52, 417; 422/83; 600/523, 600/529; 15/94, 104.03–104.05, 406, 104.061; 134/166 C, 1, 22.11–22.12
See application file for complete search history.

(56) References Cited

U.S. PATENT DOCUMENTS

| | | | | |
|---|---|---|---|---|
| 4,135,382 A | * | 1/1979 | Capone | 422/83 X |
| 4,320,528 A | * | 3/1982 | Scharton et al. | 376/310 |
| 5,123,433 A | * | 6/1992 | Fridsma et al. | 134/104.1 |
| 5,178,022 A | * | 1/1993 | Tomlin | 73/864.81 |
| 5,423,228 A | * | 6/1995 | Budd et al. | 73/863.81 X |
| 5,566,649 A | * | 10/1996 | Norris | 122/379 |
| 6,399,391 B1 | * | 6/2002 | Tomlin | 422/83 X |
| 6,474,350 B1 | * | 11/2002 | Mizuta | 134/56 R |
| 6,736,883 B2 | | 5/2004 | Sjostrom et al. | |
| 2005/0084976 A1 | | 4/2005 | Baldwin et al. | |
| 2006/0179946 A1 | * | 8/2006 | Wilson | 73/570 |
| 2007/0193374 A1 | * | 8/2007 | Shimada et al. | 73/863.21 |
| 2008/0282764 A1 | * | 11/2008 | Holt et al. | 73/23.31 X |
| 2009/0000349 A1 | * | 1/2009 | Holt et al. | 73/1.03 |

FOREIGN PATENT DOCUMENTS

| | | | | |
|---|---|---|---|---|
| EP | 1008842 A2 | * | 6/2000 | |
| JP | 61040537 A | * | 2/1986 | |
| JP | 62070729 A | * | 4/1987 | |

(Continued)

*Primary Examiner*—Thomas P Noland
(74) *Attorney, Agent, or Firm*—Greg Strugalski; Ernest G. Cusick; Frank A. Landgraff

(57) ABSTRACT

An apparatus for cleaning a continuous emissions monitor system that is in fluid communication with a flue stack conducting exhaust gas from a combustion source. The apparatus comprises a housing and a probe mounted in the housing. The probe is tubular and in fluid communication with the flue stack to acquire a sample of gas from the flue stack. The probe tends to have deposits from the exhaust gas accumulate on the inner walls of the probe. A device imparts cleaning energy to the probe for dislodging accumulated deposits from the inner walls of the probe.

12 Claims, 2 Drawing Sheets

FOREIGN PATENT DOCUMENTS

| JP | 2619494 | B2 | * | 6/1997 |
| JP | 2004061484 | A | * | 2/2004 |
| JP | 2004138475 | A | * | 5/2004 |
| WO | WO 2005/029044 | A1 | * | 3/2005 |
| WO | WO 2005100947 | A1 | * | 10/2005 |

* cited by examiner

CLEANING SYSTEM AND METHOD FOR CONTINUOUS EMISSIONS MONITORING EQUIPMENT

BACKGROUND OF THE INVENTION

Field of the Invention

The present invention relates generally to continuous emissions monitoring of exhaust flue gas streams. More specifically, the present invention relates to cleaning components of continuous emissions monitoring equipment.

The United States Environmental Protection Agency (EPA) identifies sources of mercury emissions in the U.S. to be utility boilers, waste incinerators which burn mercury-containing wastes (municipal and medical), coal-fired industrial boilers and cement kilns that burn coal-based fuels. A particularly significant source of mercury emissions is coal-fired power plants.

To quantify the emissions from a source, a mercury continuous emissions monitoring system (CEMS) is employed. There are basically three forms of mercury in exhaust flue gas stream of a coal fired power plant that may be monitored by a CEMS. These forms are gaseous elemental mercury, gaseous oxidized mercury and particulate bound mercury of either form, at stack gas temperatures in excess of 200° F.

Mercury in the gaseous forms is relatively sticky and has a strong affinity to attach to a wide variety of interior surfaces of a CEMS components. Such gaseous mercury is extremely difficult to handle and transport through an extractive gas sampling system to a gas analyzer for measurement. Furthermore, particulate present in coal fired power plants exhaust flue streams tends to absorb gaseous mercury especially when it accumulates in the CEMS sample transport system and probe. Since exhaust flue gases usually contain relatively low levels of gaseous mercury that must be detected, the small amount of gaseous mercury present that readily attaches to surfaces of the CEMS renders any measurement made on the sample not truly representative of what is conducted in the exhaust stack.

More restrictive controls on mercury mandated by the EPA will likely result in higher operational costs to flue gas generators, such as coal-fired plant owners. Accordingly, there exists a real and eminent need for the development of a durable, low cost, accurate technology capable of measuring mercury emitted in an exhaust flue gas stream in real-time. A total mercury measurement is required for regulatory monitoring, whereas the evaluation of mercury control technologies and manufacturing processes requires accurate measurements of gaseous mercury.

SUMMARY OF THE INVENTION

One aspect of the present invention is directed to an apparatus for cleaning a continuous emissions monitor system (CEMS) that is in fluid communication with a flue stack conducting exhaust gas from a combustion source. The apparatus comprises a housing and a probe mounted in the housing. The probe and other components in fluid communication with the flue stack to acquire a sample of gas from the flue stack are tubular. The probe and other components tend to have deposits from the exhaust gas accumulate on the inner walls of the probe and components. A device is provided according to aspects of the invention for imparting cleaning energy to the probe and components for dislodging accumulated deposits from the inner walls of the probe and components.

Another aspect of the present invention is directed to a method of cleaning a continuous emissions monitor system that is in fluid communication with a flue stack conducting exhaust gas from a combustion source. The method comprises the steps of providing a tubular probe in fluid communication with the flue stack to acquire a sample of gas from the flue stack. The probe tends to have deposits from the exhaust gas accumulate on the inner walls of the probe. Cleaning energy is imparted to the probe for dislodging accumulated deposits from the inner walls of the probe.

DETAILED DESCRIPTION OF THE INVENTION

A mercury continuous emissions monitoring system (CEMS) normally consists of a tubular probe assembly located in fluid communication with a flue stack for acquiring an exhaust gaseous sample. The CEMS also includes instrumentation located some distance away from the probe assembly to analyze the acquired sample for the presence of mercury. The amount of mercury present in the exhaust gas stream is continuously measured and recorded. Over time, the total amount of mercury emitted is established. A critical component of the mercury CEMS is the tubular probe assembly located in fluid communication with the stack for taking the sample.

The tubular probe assembly experiences multiple problems. Particulate matter and moisture, which are always present in the in the exhaust stack gas stream, tend to accumulate on the inner wall of the tubular probe assembly which can clog components of the probe assembly. A clogged probe assembly reduces the accuracy of the mercury measurement or ceases measurement completely. Clogging of the probe assembly can result in a reduction of the amount of time the mercury CEMS is accurately measuring emissions in the exhaust gas stream that is mandated by governmental regulation.

The probe assembly is generally U-shaped with an inlet and outlet. An initial filter may or may not be located near the inlet of the probe assembly from which gas samples are drawn from. A venturi eductor is located near the outlet and is supplied by a source of clean heated air which exits from the gas outlet into the exhaust stack gas stream.

This flow of eductor air generates a high velocity (70-100 feet per second) gas flow through the probe assembly, creating a vacuum at the gas inlet. This vacuum at the gas inlet draws the sample stack gas into the probe assembly. Experience has shown that despite the high flow rate, particulate matter does deposit within the probe assembly, especially in the presence of high moisture content in the stack gas. This causes inaccuracies of the measurement of mercury in the exhaust gas stream, increasing maintenance and down time.

Figure 1:
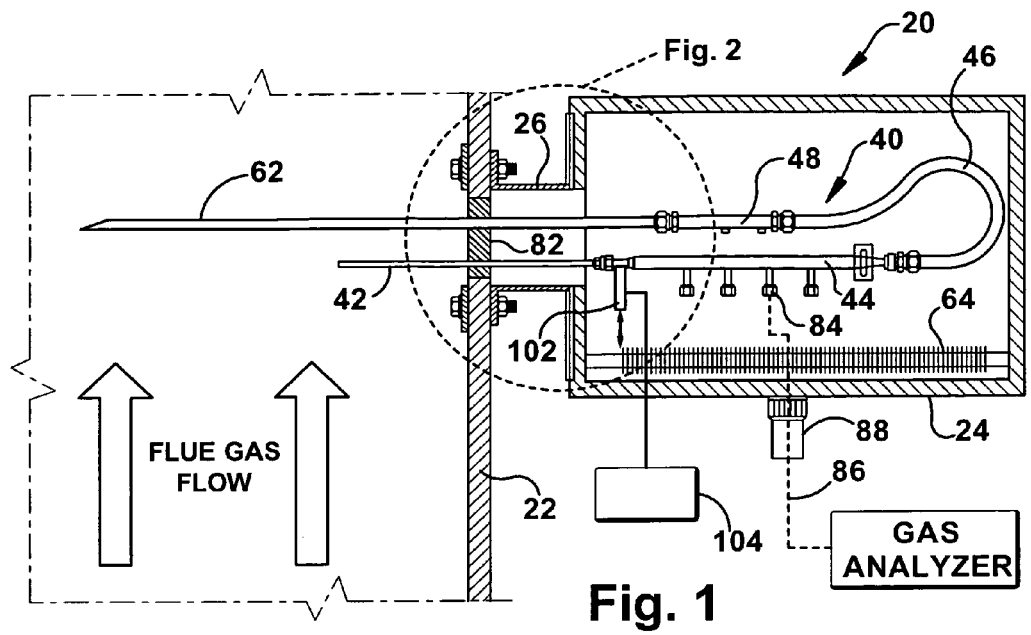
FIG. 1 is a schematic illustration, partly in section, of a cleaning system, according to one aspect of the invention, for a continuous emissions monitor.
Figure 2:
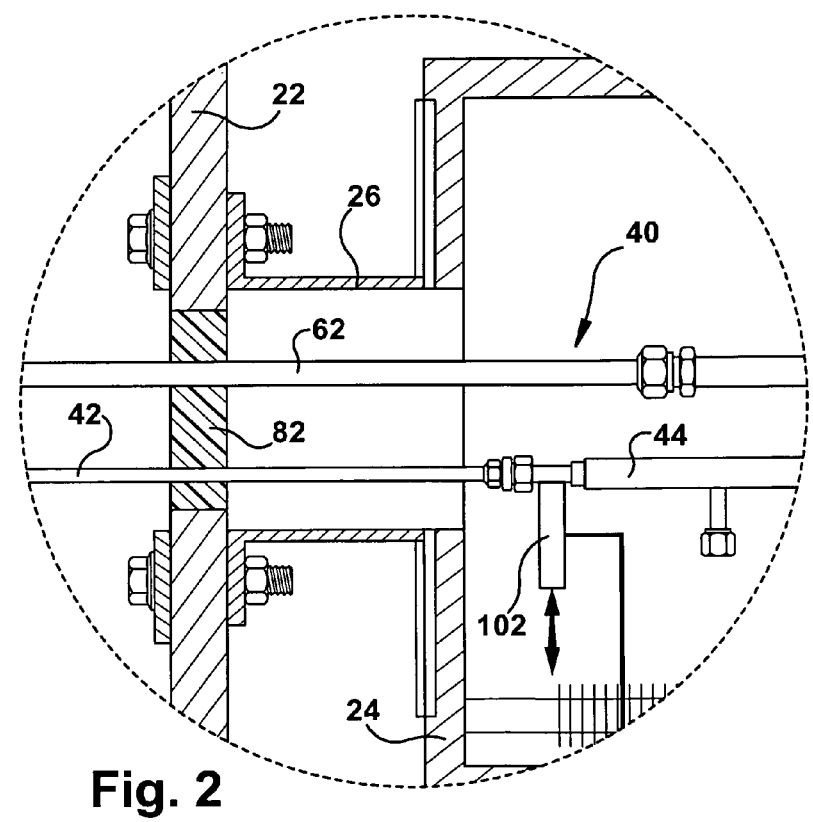
FIG. 2 is an enlarged view of a portion the cleaning system of FIG. 1.

A gas sample acquisition apparatus 20 is illustrated in FIG. 1, and includes structure according to one aspect of the invention to clean at least some of its components. The gas sample acquisition apparatus 20 is part of a continuous emissions monitoring system (CEMS) and is operatively connected with a known gas analyzer. Such a gas sample acquisition apparatus 20 and CEMS is suitable for sampling desired pollutants, such as mercury, that is transported in a flue gas stream flowing in an exhaust stack 22 from a combustion source.

The gas sample acquisition apparatus 20 includes a housing 24. The housing 24 is made to comply with NEMA standards and is insulated. The housing 24 is attached to the exhaust stack 22 by a tubular connector 26.

Since the tubular probe assembly is mounted on the exhaust stack, access to the probe and therefore maintenance of the probe assembly is difficult and time consuming. It is desirable that the probe assembly be as reliable and maintenance-free as possible.

The gas sample acquisition apparatus 20 also includes a probe assembly 40 mounted in the housing 24. Components of the probe assembly 40 are tubular. The probe assembly 40 includes an inlet or probe tip 42 that is in fluid communication with the flue gas stream in the exhaust stack 22. The probe tip 42 is connected to an inertial filter 44 of the probe assembly 40. The inertial filter 44 is attached to a generally U-shaped stainless steel return pipe 46. The stainless steel return pipe 46 is attached to a venturi flow meter 48. The venturi flow meter 48 is connected to an outlet or eductor 62 that is open to the flue gas flow. The temperature of the gas sample within the components of the probe assembly 40 located in the housing 24 is maintained via a block or jacket heater 64.

The probe tip 42 extends into the exhaust stack 22 through flexible thermal insulation 82. The probe tip 42 draws a sample from the exhaust flue gas flow. The gas sample is transported into the inertial filter 44. The gas sample leaves the inertial filter 44 via the stainless steel return pipe 46. The gas sample then passes through the venturi flow meter 48. Finally, the gas sample leaves the component housing 24 by passing through the eductor 62. The gas sample is extracted from the gas sample acquisition apparatus 20 via a sample pump (not shown) and a valve (not shown).

During the circulation of the gas sample through the components of the probe assembly 40, a representative sub-sample is drawn from the inertial filter 44 at tap 84. The sub-sample is conducted out of the housing 24 in line 86 extending through port 88. The sub-sample is conducted to a gas analyzer for analysis in a known manner. Suitable gas analyzers are well known in the art and include, without limitation, UV atomic absorption and atomic fluorescence detectors.

It is desirable, but not required, to keep the components of the probe assembly 40 at around 200° C. to ensure optimum accuracy in the measurement of total gaseous mercury concentration. The entire flow path throughout the tubular components of the probe assembly 40 is relatively smooth, with no gaps in the tubing of the assembly where particulate material might collect. Accordingly, the components provide, a consistently laminar flow of the sample through the tubular components of the probe assembly 40 in contact with the flue gas sample. The size and porosity of the inertial filter 44 and other components are selected to provide the desired flow of the gas sample through the components of the probe assembly 40.

To minimize particulate matter from accumulating and depositing within the components of the probe assembly 40 of the gas sample acquisition apparatus 20 is the addition of a cleaning device 102 to periodically or continually shake or vibrate the components. The cleaning device 102 is mounted to the housing 24 and operatively attached to the component of the probe assembly 40. The force applied by the cleaning device at the proper frequency and magnitude causes any agglomerated particulate material to dislodge from the interior walls of the tubular components of the probe assembly 40. The dislodged particulate material will break into finer particles which will be discharged into the stack's gas flow, thus yielding a clean probe assembly 40. Thus, the probe assembly 40 is relatively maintenance free and provides a representative sample from the exhaust flue gas flow.

Any means of shaking, vibrating, or otherwise mechanically exciting the interior surfaces of the components of the probe assembly 40 are contemplated by this invention so other traditional and labor intensive means of cleaning the probe assembly (for example, brushes) would not have to be implemented. Particulate matter does not stick to the interior surfaces of the components of the probe assembly 40 upon the application of appropriate predetermined vibratory force and frequency. The vibratory force can be applied periodically, continually, or in concert with the additional cleaning air. The cleaning device 102 is connected to a controller 104. The controller 104 establishes when the cleaning device 102 is activated, the duration of actuation, the intensity of actuation and frequency of activation.

The vibratory or shaking force can be supplied by either an electrical, mechanical or pneumatic cleaning device 102. An example of the cleaning device 102 would be the addition of a silent pneumatic turbine vibrator, model number VS-160, as manufactured by Vibco of Wyoming, R.I. While the cleaning device 102 is illustrated as attached to the probe assembly 40 at the inertial filter and applying a reciprocal vertical cleaning force, it may be operatively connected with any component of the probe assembly 40 and apply any suitable force.

Figure 3:
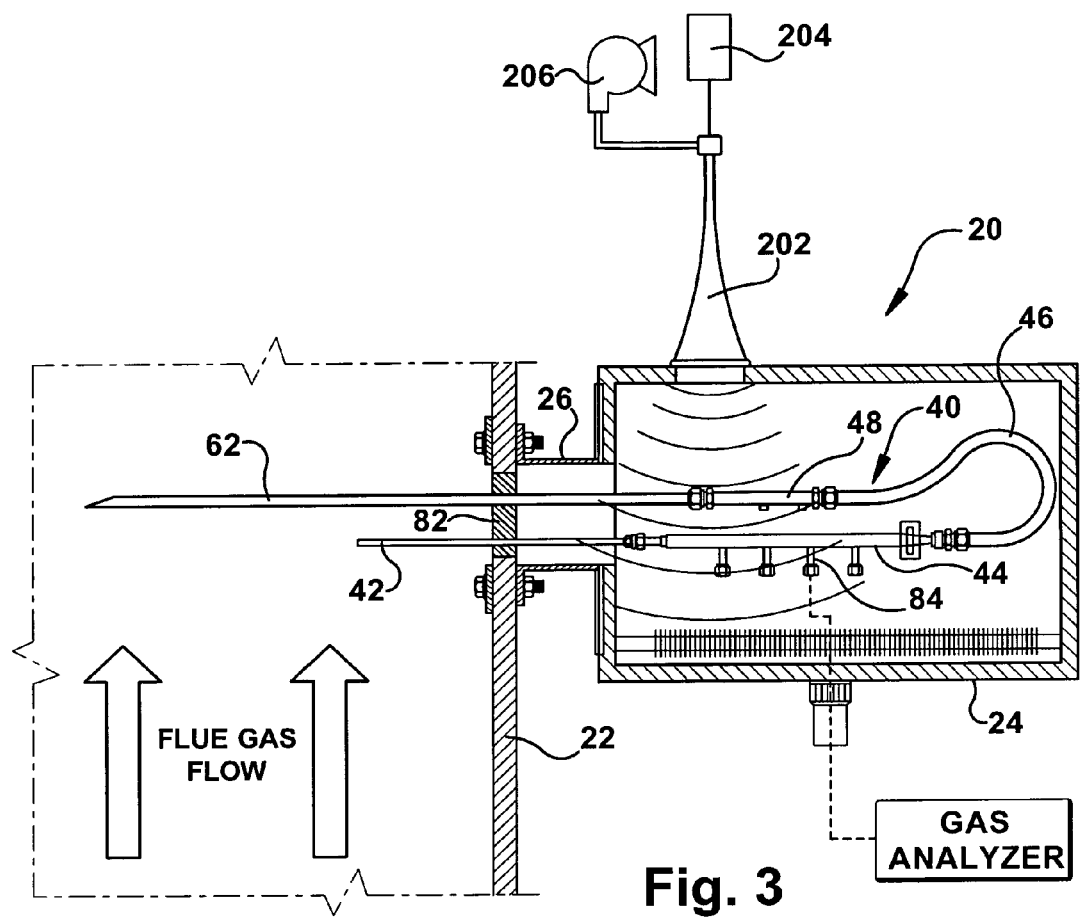
FIG. 3 is a schematic illustration, partly in section, of a cleaning system, according to another aspect of the invention, for a continuous emissions monitor.

A gas sample acquisition apparatus 20 is illustrated in FIG. 3, and includes structure according to another aspect of the invention to clean its components. The gas sample acquisition apparatus 20 is part of a continuous emissions monitoring system (CEMS) and is operatively connected with a known gas analyzer. Such a gas sample acquisition apparatus 20 and CEMS is suitable for sampling desired pollutants, such as mercury, that is transported in a flue gas stream flowing in an exhaust stack 22.

The gas sample acquisition apparatus 20 includes the housing 24. The housing 24 is attached to the exhaust stack 22 by the tubular connector 26. The probe assembly 40 includes the probe tip 42 connected to the inertial filter 44. The inertial filter 44 is attached to the return pipe 46. The return pipe 46 is attached to the venturi flow meter 48. The venturi flow meter 48 is connected to the eductor 62 that is open to the flue gas flow. The temperature of the components of the gas sample acquisition apparatus 20 is maintained via a block or jacket heater 64.

The probe tip 42 extends into the exhaust stack 22 through flexible thermal insulation 82. The probe tip 42 draws a sample from the exhaust flue gas flow. The gas sample is transported into the inertial filter 44. The gas sample leaves the inertial filter 44 via the stainless steel return pipe 46. The gas sample then passes through the venturi flow meter 48. Finally, the gas sample leaves the housing 24 by passing through an eductor 62. The gas sample is extracted from the gas sample acquisition apparatus 20 via a sample pump (not shown) and a valve (not shown).

During the circulation of the gas sample through the components of the probe assembly 40, a representative sub-sample is drawn from the inertial filter 44 at tap 84. The sub-sample is conducted out of the housing 24 in line 86 extending through port 88. The sub-sample is conducted to the gas analyzer for analysis in a known manner.

To minimize particulate matter from depositing within the components of the probe assembly 40 of the CEMS a cleaning device 202 periodically or continually applies acoustic cleaning energy to the components of the probe assembly. The cleaning device 202 is in the form of an acoustic horn, available from BHA Group, Inc. in Kansas City, Mo. Upon the application of sufficient force by the cleaning device 202 at a proper frequency, agglomerated particulate material will dislodge from the interior walls of the components of the probe assembly 40. The dislodged particles which will be discharged into the stack's gas flow, thus yielding a clean gas sample acquisition apparatus 20.

The cleaning device 202 is illustrated as mounted to the top of the housing 24 and direct sound waves downwardly through an opening in the housing at the components of the probe assembly 40. The cleaning device 202 may be mounted anywhere on the housing 24 and in any orientation to deliver effective acoustic energy at the components of the probe assembly 40.

The acoustic vibratory or shaking force can be applied periodically, continually, or in concert with the additional cleaning air. The cleaning device 202 is connected to a controller 204 and an air supply 206 for the cleaning device 202. The controller 204 establishes when the cleaning device 202 is activated to deliver acoustical energy, the duration of actuation, the intensity of actuation and frequency of activation.

While the invention has been described in terms of various specific embodiments, those skilled in the art will recognize that the invention can be practiced with modification within the spirit and scope of the claims.

What is claimed is:

1. An apparatus for cleaning a continuous emissions monitor system that is in fluid communication with a flue stack conducting exhaust gas from a combustion source, the apparatus comprising:
    a housing;
    a probe mounted in the housing, the probe being tubular and defined by an inner wall, the probe being in fluid communication with the flue stack to acquire a sample of gas from the flue stack, the probe tending to have deposits from the exhaust gas accumulate on the inner wall of the probe; and
    a device for imparting cleaning energy to the probe for dislodging accumulated deposits from the inner wall of the probe while the probe remains in operational fluid communication with the flue stack, all probe cleaning energy is in the form of probe vibration and is imparted by the device from outside of the probe.

2. The apparatus of claim 1 wherein the device is a mechanism connected with the probe and the cleaning energy imparted to the probe is mechanical.

3. The apparatus of claim 1 wherein the device is an acoustic horn and the cleaning energy imparted to the probe is acoustical.

4. The apparatus of claim 1 further including a controller operatively connected with the device to control the application of cleaning energy.

5. An apparatus for cleaning gas acquisition components of a continuous emissions monitor system that is in fluid communication with a flue stack conducting an exhaust gas from a combustion source, the apparatus comprising:
    tubular components in fluid communication with the flue stack to acquire a sample of gas from the flue stack, the tubular components tending to have deposits from the exhaust gas accumulate on the inner wall of the tubular components; and
    a device for imparting cleaning energy to the tubular components for dislodging accumulated deposits from the inner wall of the tubular components while the tubular components remain in operational fluid communication with the flue stack, all probe cleaning energy is in the form of probe vibration and is imparted by the device from outside of the probe.

6. The apparatus of claim 5 wherein the device is a mechanism connected with the probe and the cleaning energy applied to the tubular components is mechanical.

7. The apparatus of claim 6 further including a controller operatively connected with the device to control the application of cleaning energy.

8. The apparatus of claim 5 wherein the device is an acoustic horn and the cleaning energy applied to the tubular components is acoustical.

9. A method of cleaning a continuous emissions monitor system that is in fluid communication with a flue stack conducting exhaust gas from a combustion source, the method comprising the steps of:
    providing a tubular probe defined by an inner wall in fluid communication with the flue stack to acquire a sample of gas from the flue stack, the probe tending to have deposits from the exhaust gas accumulate on the inner wall of the probe; and
    imparting cleaning energy to the probe for dislodging accumulated deposits from the inner wall of the probe while the probe remains in operational fluid communication with the flue stack, all probe cleaning energy is in the form of probe vibration and is imparted by the device from outside of the probe.

10. The method of claim 9 wherein the cleaning energy imparted to the probe is mechanical.

11. The method of claim 9 wherein the cleaning energy imparted to the probe is acoustical.

12. The method of claim 9 further including the step of controlling the application of cleaning energy.

* * * * *